United States Patent [19]

Milev

[11] 4,261,951
[45] Apr. 14, 1981

[54] APPARATUS FOR BLOOD OXYGENATION

[75] Inventor: Milan H. Milev, Sofia, Bulgaria

[73] Assignee: DSD "Metalchim", Sopot, Bulgaria

[21] Appl. No.: 19,552

[22] Filed: Mar. 12, 1979

[51] Int. Cl.³ ............................................. A61M 1/03
[52] U.S. Cl. ............................... 422/46; 128/DIG. 3; 422/47
[58] Field of Search .............. 422/46, 47; 128/DIG. 3

[56] References Cited

U.S. PATENT DOCUMENTS

| | | | |
|---|---|---|---|
| 2,934,067 | 4/1960 | Calvin | 422/46 |
| 3,291,568 | 12/1966 | Sautter | 422/46 |
| 3,488,158 | 1/1970 | Bentley et al. | 422/46 X |
| 3,764,271 | 10/1973 | Brumfeld | 422/46 |
| 3,768,977 | 10/1973 | Brumfeld et al. | 422/46 |
| 3,769,162 | 10/1973 | Brumfeld | 422/46 X |
| 3,807,958 | 4/1974 | Brumfeld et al. | 422/46 |
| 3,898,045 | 8/1975 | Bowley | 422/46 |
| 3,994,689 | 11/1976 | DeWall | 422/47 X |
| 4,073,622 | 2/1978 | Luppi | 422/47 |
| 4,138,288 | 2/1979 | Lewin | 422/46 X |
| 4,138,464 | 2/1979 | Lewin | 422/46 |
| 4,140,635 | 2/1979 | Desmond | 422/46 X |

FOREIGN PATENT DOCUMENTS 1398818 6/1975 United Kingdom .
1430226 3/1976 United Kingdom .
1503595 3/1978 United Kingdom .

Primary Examiner—Barry Richman
Attorney, Agent, or Firm—Karl F. Ross

[57] ABSTRACT

An apparatus for the oxygenation of blood has a housing centered on an upright axis and an oxygenation chamber below the housing which has a tube formed thereon which extends upwardly and passes coaxially through the housing, the chamber communicating therewith through the tube. Provided in the housing is a microporous shell which surrounds the tube and defines with it a defoaming chamber into which the tube feeds, the shell also defining with the housing a reservoir for the oxygenated blood. A heat exchanger is provided in the oxygenation chamber surrounding a flow-directing body, while a vertically disposed oxygen inlet pipe having a diffusion nozzle is provided in the bottom of the chamber with a pair of blood inlet pipes flanking the oxygen pipe and forming an angle therewith.

7 Claims, 1 Drawing Figure

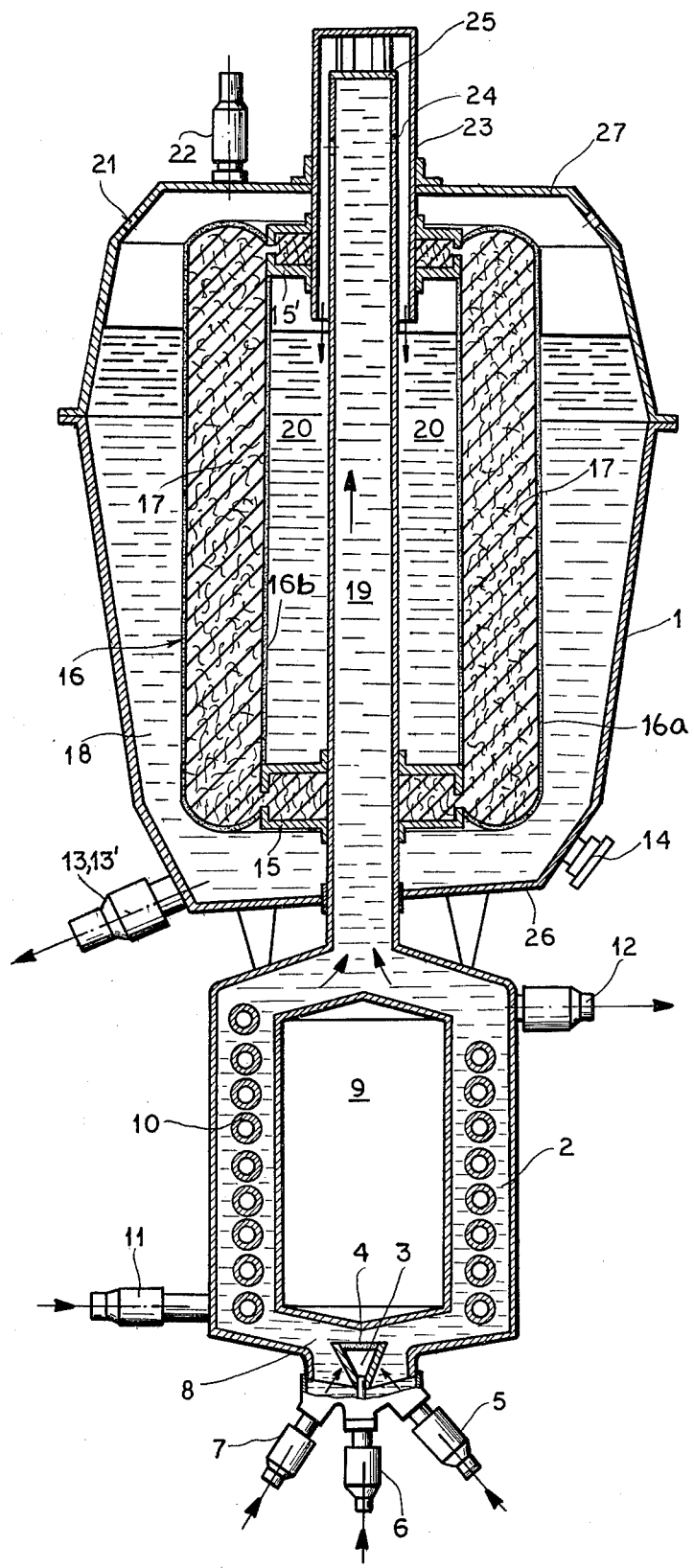

APPARATUS FOR BLOOD OXYGENATION

FIELD OF THE INVENTION

This invention relates to an apparatus for blood oxygenation oxygening during surgical procedures.

BACKGROUND OF THE INVENTION

An apparatus for blood oxygenation is known, which comprises a chamber for oxygen, over which there is disposed a chamber for the blood. Both chambers are connected by passageways, through which the oxygen passes under pressure. Over the chamber for the blood there is a bundle of pipes, through which the blood and the oxygen pass, the blood being saturated with oxygen. Over the pipes there is disposed a gas-distributing chamber, through the openings of which the foamed blood passes into a defoaming cylindrical space, containing a microporous material covered by a thin silicon layer. The microporous material envelops part of the upper end of the bundle of oxidizing pipes.

The defoaming cylindrical space and the gas distribution chamber are surrounded by a thin blood filter, concentrically to which there is disposed a conduit for the circulating blood containing a heat-exchange pipe. Beneath the defoaming bed there is disposed the blood reservoir, in which the oxygenated blood is collected.

The disadvangage of this apparatus is that the direct contact between the oxygen and the venous blood takes place at a comparatively high pressure, thus resulting in the traumation of a large portion of the blood elements. This high pressure is determined by the resistance which must be overcome by the blood when it passes through the bundle of pipes, the diameter of which is relatively small, causing an intensive foaming of the blood which is undesirable.

To achieve a defoaming of the thus abundantly foamed blood, it is passed through a porous material, saturated with silicone or enveloped by a thin silicone layer, which combines with the blood elements and is introduced with the oxygen-saturated blood into the human body. The silicone compound causes a postperfusion syndrome, due to the so-called silicone embolism, causing a harmful influence on the central nervous system. A large portion of the blood elements are destroyed as a result of their high velocity during the saturation with oxygen and the interaction with the silicone compound, and they cannot serve their physiological purpose.

OBJECTS OF THE INVENTION

It is, therefore, a general object of the present invention to provide an apparatus for blood oxygenation, which causes minimum traumas to the blood elements, and avoids the use of silicione compounds as defoaming agents.

SUMMARY OF THE INVENTION

This object is achieved by an apparatus comprising a housing, generally cylindrical along the axis of which there is disposed a cylindrical oxygenation chamber and tube. Around the oxygenation tube, which extends into the housing, there is provided a defoaming chamber formed by a surrounding shell of microporous material, enveloped by a microporous filter. A reservoir for oxygenated blood is formed by the walls of the housing. In the base of the oxygenation chamber there is disposed a diffusion nozzle for oxygen, mounted coaxially with respect to the oxygenation chamber and connected to an inlet pipe for oxygen. Two inlet pipes for blood are disposed in the base of the oxygenation chamber at an angle with respect to the pipe for blood. In the center of the oxygenation chamber there is a hollow body, around which a helically shaped heat-exchanger is rigidly fixed. On the upper end of the oxygenation chamber there is mounted the oxygenation tube, which passes through the housing. The upper end of the oxygenation tube extends above the cover of the housing. To the cover of the housing there is rigidly fastened a covering sleeve, disposed at a certain distance above and around the upper end of the oxygenation tube. In the lower end of the covering sleeve and the oxygenation tube there is provided a fixing collar, in peripherial holes of which are attached both ends of the microporous shell. The ratio of the cross-sectional area of the oxygenation chamber to the cross-sectional area of the housing is preferably 1:4. The ratio of the cross-sectional area of the oxygenation tube to the cross-sectional area of the oxygenation chamber is about 1:2.

The apparatus for blood oxygenation in accordance with the present invention has the following advantages: the saturation of venous blood with the necessary quantity of oxygen is achieved at a minimum velocity of flow of the blood and a minimum pressure of the oxygen, this resulting in a minimum foaming of the blood, thus avoiding the necessity of using a silicone defoaming compound; the minimum speed of saturation of the blood with oxygen allows a minimum traumation of the blood elements, this resulting in an arterial blood with preserved maximum physiological properties.

BRIEF DESCRIPTION OF THE DRAWING

For a better understanding of the invention, reference should be made to the accompanying drawing, in the sole Figure of which there is illustrated and described a preferred embodiment of the invention. The drawing is a cross-sectional view through an apparatus in accordance with the invention.

SPECIFIC DESCRIPTION

The apparatus for blood oxygenation comprises a housing 1 through which an oxygenation tube 19 passes, which is connected at its bottom end, outside housing 1, to an oxygenation chamber 2. In the center of the base of the oxygenation chamber 2 and coaxial with it there is disposed a pipe 6 for oxygen supply. The upper end of this oxygen-supply pipe 6 widens conically to form a diffusion nozzle 3 the outlet end of which is covered by a microporous plate 4.

The latter forms the flat horizontal top of the upwardly diverging conical device nozzle 3, this top being spaced but close to the conical lower face of the body 9 above this nozzle. The nozzle has a conical lower face surrounded by the neck of chamber 2. On both sides of the oxygen pipe 6 there are mounted at an angle of 45° with respect to it, a pipe 5 for coronary blood and a pipe 7 for venous blood. In the center of the oxygenation chamber 2, at equal distances from its walls, there is disposed a flowing direction hollow body 9, around which there is fastened rigidly a helically-shaped heat-exchanger 10. The inlet pipe 11 and the outlet pipe 12 of the helically-shaped heat-exchanger 10 are located in the bottom and the upper end of the oxygenation chamber, respectively.

The oxygenation tube 19 begins at the upper end of the oxygenation chamber 2, and extends along the axis and through the whole housing, its upper end extending above the cover 27 of housing 1. The tube 19 is closed at the upper end by a cover plate 25, underneath of which there are provided six orifices 24 along the periphery of the oxygenation tube 19. Over and around the upper portion of tube 19 there is provided a covering sleeve 23, which is fastened rigidly to the cover 27 of housing 1. To the lower portion of the covering sleeve 23 there is fastened a fixing collar 15′, and attached rigidly to the lower portion of oxygenation tube 19, a fixing collar 15 collar 15 and 15′ holding a microporous shell 17 in position on tube 19. The microporous shell 17 is fixed at both ends by respective fixing collars 15 and 15′ and is enveloped from inside and outside by a filter net 16 with a pore size of from 30 to 80 microns, equal to those of the microporous material of shell 17, the thickness of which is from 15 to 30 mm. The microporous shell is disposed concentrically to the oxygenation tube 19 and at a preset distance from the bottom and the cover of housing 1 and defines with tube 19 a concentric deforming chamber 20.

Between the outer surface of the microporous shell 17 and the casing of housing 1 there is defined an arterial reservoir 18 with inclined bottom 26. In the lower part of this inclined bottom there are disposed outlet pipes 13 and 13′ for feeding oxygenated blood to the arterial and coronary portions of the circulatory system. Diametrically opposite to them there is an outlet 14 for taking blood samples. The cover 27 of housing 1 is provided with a pipe connection 22 for introducing blood or other liquids. Along the periphery of cover 27 there are four openings 21, through which the separated carbon dioxide and the excess oxygen are released.

The apparatus operates as follows. The venous and the coronary blood pass through pipe 7 for venous blood and pipe 5 for coronary blood, respectively; they flow into a mixing chamber 8 formed at the botton of chamber 2 and cover the oxygen diffusion nozzle chamber 3. Oxygen enters the nozzle 3 through the oxygen pipe 6 in a ratio of 0.5 to 1 to the blood. The bubbled blood rises up in the oxygenation chamber 2, passing around the heat-exchanger 10 and through the oxygenation tube 19 and the orifices 24 in its upper end, flowing into the covering sleeve 23 and then into the defoaming chamber 20. From here the blood passes through the internal layer 16a of the filter net 16, the microporous shell 17 and the outer layer 16b of filter net 16. The blood bubbles are broken-up, and the residual oxygen and carbon dioxide separated. The thus separated gas is directed towards the upper end of housing 1 and reaches the atmosphere through openings 21.

The defoamed blood flows down along the exterior of shell 17 and is collected in the bottom of arterial reservoir 18. From there, it is directed through outlet pipes 13 and 13′ to the circulatory system of the human body.

What we claim is:

1. An apparatus for blood oxygenation comprising:
a housing centered on an upright axis;
an oxygenation tube passing coaxially through said housing;
an oxygenation chamber having an upwardly diverging frustoconical bottom formed at the lower end of said tube beneath said housing and communicating therewith through said tube;
an elongated upright flow-directing body positioned in said oxygenation chamber having a conical lower face with an upward divergence spaced from the frustoconical bottom of said oxygenation chamber;
a heat exchanger surrounding said body;
a mixing chamber defined between said body and said bottom of said oxygenation chamber;
a vertically disposed oxygen inlet pipe provided in the bottom of said oxygenation chamber, said bottom being formed with a downwardly extending neck;
an upwardly diverging conical diffusion nozzle having a flat horizontal top closely spaced from said conical lower face provided on said oxygen inlet pipe in said mixing chamber, said nozzle having a conical surface coaxially surrounded by and spaced from said neck;
a pair of blood inlet pipes provided in the bottom of said oxygenation chamber disposed on either side of said oxygen inlet pipe at an angle thereto and directed toward the conical surface of said diffusion nozzle while opening into the space between said neck and said surface;
a shell of microporous material in said housing surrounding said tube and defining therewith a defoaming chamber, said tube feeding thereinto;
a filter net of microporous material covering at least the exterior surfaces of said shell; and
a reservoir defined between said shell and said housing for collecting the oxygenated blood.

2. An apparatus for blood oxygenation comprising:
a housing centered on an upright axis;
an oxygenation tube passing coaxially through said housing;
an oxygenation chamber formed at the lower end of said tube beneath said housing and communicating therewith through said tube;
a flow-directing body positioned in said oxygenation chamber;
a heat exchanger surrounding said body;
a mixing chamber defined between said body and the bottom of said oxygenation chamber;
a vertically disposed oxygen inlet pipe provided in the bottom of said oxygenation chamber;
a diffusion nozzle provided on said oxygen inlet pipe in said mixing chamber;
a pair of blood inlet pipes provided in the bottom of said oxygenation chamber disposed on either side of said oxygen inlet pipe at an angle thereto;
a shell of microporous material in said housing surrounding said tube and defining therewith a defoaming chamber, said tube feeding thereinto;
a filter net of microporous material covering at least the exterior surfaces of said shell; and
a reservoir defined between said shell and said housing for collecting the oxygenated blood and said oxygenation tube extending beyond the top of said housing and provided with a plurality of orifices formed in the periphery at the upper end thereof and a sleeve closed at the upper end thereof mounted on said housing and centered on said upright axis, said sleeve being telescopically positioned over the upper end of said tube in a spaced-apart relationship therewith and extending downwardly into said defoaming chamber for directing the oxygenated blood from the upper end of said tube into said defoaming chamber.

3. The apparatus defined in claim 2 wherein the ratios of the cross-sectional areas of said oxygenation chamber to said housing and said tube are 1:4 and 2:1 respectively.

4. The apparatus defined in claim 2 wherein the pore size of the microporous material of said shell and said filter net is from 30 to 80 microns and the wall thickness of said shell is from 15 to 30 mm.

5. The apparatus defined in claim 2, further comprising a pair of outlet pipes provided in said housing for feeding the oxygenated blood from said reservoir to the arterial and coronary portions of the circulatory system respectively and a plurality of openings formed in said housing for releasing the separated carbon dioxide and excess oxygen.

6. An apparatus for blood oxygenation comprising:
   a housing centered on an upright axis;
   an oxygenation tube passing coaxially through said housing;
   an oxygenation chamber formed at the lower end of said tube beneath the housing and communicating therewith through said tube;
   a flow-directing body positioned in said oxygenation chamber;
   a heat exchanger surrounding said body;
   a mixing chamber defined between said body and the bottom of said oxygenation chamber;
   a vertically disposed oxygen inlet pipe provided in the bottom of said oxygenation chamber;
   a diffusion nozzle provided on said oxygen inlet pipe in said mixing chamber;
   a pair of blood inlet pipes provided in the bottom of said oxygenation chamber disposed on either side of said oxygen inlet pipe at an angle thereto;
   a shell of microporous material in said housing surrounding said tube and defining therewith a defoaming chamber, said tube feeding thereinto;
   a filter net of microporous material covering at least the exterior surfaces of said shell;
   a reservoir defined between said shell and said housing for collecting the oxygenated blood, the ratios of the cross-sectional areas of said oxygenation chamber to said housing and said tube being 1:4 and 2:1 respectively, the pore size of the microporous material of said shell and said filter being from 30 to 80 microns and the wall thickness of said shell being from 15 to 30 mm; and
   a pair of outlet pipes provided in said housing for feeding the oxygenated blood from said reservoir to the arterial and coronary portions of the circulatory system respectively and a plurality of openings formed in said housing for releasing the separated carbon dioxide and excess oxygen and said oxygenation tube extends beyond the top of said housing and is provided with a plurality of orifices formed in the periphery at the upper end thereof and a sleeve closed at the upper end thereof is mounted on said housing and centered on said upright axis, said sleeve being telescopically positioned over the upper end of said tube in a spaced-apart relationship therewith and extending downwardly into said defoaming chamber for directing the oxygenated blood from the upper end of said tube into said defoaming chamber.

7. The apparatus defined in claim 6 wherein said housing is formed by a body of revolution with the bottom thereof being inclined toward said outlet pipes and said oxygenation chamber is cylindrical and lies in axial alignment with said housing.

* * * * *